United States Patent [19]
McDonald

[11] Patent Number: 6,096,731
[45] Date of Patent: *Aug. 1, 2000

[54] METHOD FOR PREVENTING TISSUE DAMAGE ASSOCIATED WITH GRAFT-VERSUS-HOST OR HOST-VERSUS-GRAFT DISEASE FOLLOWING TRANSPLANTATION

[75] Inventor: George B. McDonald, Bellevue, Wash.

[73] Assignee: Institute for Drug Research, Inc., New York, N.Y.

[*] Notice: This patent issued on a continued prosecution application filed under 37 CFR 1.53(d), and is subject to the twenty year patent term provisions of 35 U.S.C. 154(a)(2).

[21] Appl. No.: 09/151,388

[22] Filed: Sep. 10, 1998

Related U.S. Application Data

[63] Continuation-in-part of application No. 09/103,762, Jun. 24, 1998.

[51] Int. Cl.⁷ .......................... A61K 31/58; A61K 31/56; A01N 45/00
[52] U.S. Cl. .......................... 514/169; 514/170; 514/171; 514/177; 514/178; 514/179; 514/180; 514/181; 514/182; 428/451; 428/464; 428/489; 428/490
[58] Field of Search .................................. 514/169, 170, 514/171, 177, 178, 179, 180, 181, 182, 885; 428/451, 464, 489, 490

[56] References Cited

U.S. PATENT DOCUMENTS 5,403,833  4/1995  Calne ........................................ 514/171

OTHER PUBLICATIONS

"Oral Beclomethasone Diproprionate for Treatment of Human Intestinal Graft–Versus Host Disease", Baehr et al, Transplantation 60:1231–1238, Apr. 1995.

"Graft–Versus–Host Effect After Allogenic Hematopoietic Stem Cell Transplantation: GVHD and GVL", Nash et al, Curr. Opin. Immunol., 8(5), 674–680, Mar. 1996.

*Primary Examiner*—Frederick Krass
*Attorney, Agent, or Firm*—Ohlandt, Greeley, Ruggiero & Perle

[57] ABSTRACT

A method for preventing tissue damage associated with graft-versus-host disease in a patient having undergone hematopoietic cell transplantation, and host-versus-graft disease in a patient having undergone organ allograft transplantation. The method includes orally administering to the patient a prophylactically effective amount of a topically active corticosteroid, such as beclomethasone dipropionate, for a period of time following hematopoietic cell or organ allograft transplantation, and prior to the presentation of symptoms associated with graft-versus-host disease or host-versus-graft disease. Representative tissues includes tissue of the intestine and liver, while representative tissue damage includes inflammation thereof.

40 Claims, No Drawings

METHOD FOR PREVENTING TISSUE DAMAGE ASSOCIATED WITH GRAFT-VERSUS-HOST OR HOST-VERSUS-GRAFT DISEASE FOLLOWING TRANSPLANTATION

RELATED APPLICATION

This application is a continuation-in-part of U.S. application Ser. No. 09/103,762, filed Jun. 24, 1998.

STATEMENT OF GOVERNMENT INTEREST

This invention was made under grants from the U.S. Food and Drug Administration (FD-R-000827), and the National Institutes of Health (CA-18029 and CA-15704). The United States Government may have certain rights to this invention.

TECHNICAL FIELD

This invention is directed to the prevention of tissue damage, such as damage to the intestine or liver caused by graft-versus-host disease following hematopoietic cell transplantation, or caused by host-versus-graft disease following intestinal or liver transplantation, by oral administration of a prophylactically effective amount of a topically active cortico steroid, such as beclomethasone dipropionate (BDP).

BACKGROUND OF THE INVENTION

Acute graft-versus-host disease (GVHD) is a complication of allogeneic hematopoietic cell transplantation in which tissues of the host, most frequently the skin, liver and intestine, are damaged by lymphocytes from the donor. The risk and severity of this immune-mediated condition are directly related to the degree of mismatch between a host and the donor of hematopoietic cells. For example, GVHD develops in up to 30% of recipients of human leukocyte antigen (HLA)-matched sibling marrow, in up to 60% of recipients of HLA-matched unrelated donor marrow, and in a higher percentage of recipient of HLA-mismatched marrow. Patients with mild intestinal GVHD present with anorexia, nausea, vomiting, abdominal pain and diarrhea, whereas patients with severe GVHD are disabled by these symptoms. If untreated, symptoms of intestinal GVHD persist and often progress; spontaneous remissions are unusual. In its most severe form, GVHD leads to necrosis and exfoliation of most of the epithelial cells of the intestinal mucosa, a frequently fatal condition.

Standard initial treatment for acute GVHD includes systemic immunosuppressive agents, usually high-dose prednisone at 2 mg per kg per day added to prophylactic medications such as methotrexate, cyclosporine and tacrolimus. Prednisone achieves a complete and sustained remission of gastrointestinal symptoms in 50–70% of patients with GVHD. Patients who fail to respond receive therapy with additional immunosuppressive regimens, such as higher-dose prednisone, anti-thymocyte globulin, and investigational anti-T-cell monoclonal antibodies or immunotoxins. Unfortunately, the risks of prolonged immunosuppressive therapy are significant, especially among patients with immature marrow grafts. These risks include local and disseminated infection, the development of lymphoproliferative disease, and systemic glucocorticoid side effects such as hypothalamic-pituitary-adrenal axis suppression, myopathy, neuropsychiatric disease, and bone demineralization.

Recently, investigators have reported the results of a phase I trial of topically active corticosteroid, beclomethasone dipropionate (BDP), for the treatment of patients with intestinal GVHD (Baehr et al., *Transplantation* 60:1231–1238, 1995). In this trial, BDP capsules were given orally, 8 mg daily, half as enteric-coated capsules designed to dissolve in the alkaline pH of the upper small intestine, and half of the capsules that dissolve in the stomach. Significant improvement was found in the appetite, oral intake, nausea, and diarrhea over the course of therapy with oral BDP alone and with oral BDP added to prednisone therapy. However, the time to improvement in patients receiving BDP as monotherapy was 7–10 days, which is longer than the response usually seen with prednisone therapy.

A drawback with the above regimen is that treatment is initiated with BDP only after presentation of symptoms of intestinal GVHD, with typical patient enrollment at a mean of 58 days post-transplant (i.e., ranging from day 21–231 after transplant). The difficulty with treatment after presentation of intestinal GVHD symptoms is that significant inflammation and/or damage to the intestine has already occurred prior to initiation of therapy. Severe damage to the lining of the intestine is often fatal, as malnutrition, protein loss, and blood stream infections preclude regeneration of lining cells. This study did, however, provide evidence that oral BDP therapy was safe and effective in the treatment of mild-to-moderate intestinal GVHD, taken alone or when added to prednisone.

A related condition to GVHD is host-versus-graft disease (HVGD), also referred to as organ allograft rejection. HVGD disease may occur, for example, when a donor intestine is transplanted into a patient with a diseased intestine. In this case, cells of the patient's immune system (the host) may attack the foreign intestinal tissue (the graft). While intestinal transplantation is not routine at the present time, such techniques will likely become more common. Thus, prophylactic medications are needed to prevent HVGD for many of the reasons noted above with regard to GVHD.

While significant advances have been made with regard to the treatment of GVHD following bone marrow transplantation, there is still a need in the art for improved methods, particularly in the context of preventing the intestinal mucosal damage associated with the onset of GVHD. Such preventative methods should begin immediately following hematopoietic cell transplantation, and reduce tissue damage associated with the subsequent onset of GVHD. There is also a need for methods to prevent HVGD in the context of, for example, intestinal or liver transplantation. The present invention fulfills these needs and provides further related advantages.

SUMMARY OF THE INVENTION

In brief, this invention discloses a method for preventing tissue damage, particularly of the intestinal and/or liver, caused by graft-versus-host disease (GVHD) that commonly follows hematopoietic cell transplantation, or caused by host-versus-graft disease (HVGD) or organ allograft rejection.

Hematopoietic cell transplantation is the generic term that encompasses bone marrow transplantation, peripheral blood stem cell transplantation, umbilical vein blood transplantation, or any other source of pleuripotent hematopoietic stem cells. The method includes the oral administration of a prophylactically effective amount of a topically active corticosteroid (abbreviated herein as "TAC") to a patient having undergone hematopoietic cell transplantation.

A representative TAC of this invention is beclomethasone dipropionate (BDP). Such prophylactic administration continues for a period of time following the hematopoietic cell transplantation, thereby preventing, delaying and/or reducing severity of the symptoms normally associated with tissue damage caused by GVHD.

In one embodiment, the tissue damage is caused by intestinal inflammation associated with intestinal graft-versus-host disease in a patient having undergone hematopoietic cell transplantation. In this embodiment, a prophylactically effective amount of a TAC is orally administered to a patient in need thereof for a period of time following hematopoietic cell transplantation and prior to the presentation of symptoms of intestinal GVHD.

In another embodiment, the tissue damage is caused by HVGD or organ allograft rejection, including (but not limited to) intestinal or liver transplantation. In this embodiment, a prophylactically effective amount of a TAC is orally administered to a patient in need thereof for a period of time following transplantation and prior to presentation of symptoms of HVGD. In the case of intestinal transplantation, administration is prior to symptoms of intestinal HVGD, and in the case of liver transplantation prior to signs of liver HVGD (rejection).

In more specific embodiments, the TAC is administered orally at a dosage of 4 mg/day to 12 mg/day in a form suitable for oral administration, such as capsules, pills, coated microspheres with specific dissolution qualities, or emulsions. Other agents may optionally also be included in such oral formulations.

These and other aspects of this invention will be evident upon reference to the following detailed description.

DETAILED DESCRIPTION OF THE INVENTION

As mentioned above, this invention is directed to a method for preventing tissue damage caused by graft-versus-host disease (GVHD) which commonly follows hematopoietic cell transplantation, as well as by host-versus-graft disease (HVGD) or allograft rejection which commonly follows organ transplantation. As used herein, the term "prevent" or "prevention" means preventing, delaying and/or reducing the severity of the symptoms associated with GVHD following hematopoietic cell transplantation or HVGD following organ allograft transplantation. Prevention in the context of this invention is to be distinguished from "treatment," which occurs following the onset of the first symptom(s) of GVHD or HVGD.

In the context of this invention, "tissue" means intestinal mucosa or the small bile ducts in the liver. Intestinal mucosa includes mucosa of the esophagus, stomach, small intestine and colon. "Damage" to such tissue may range from mild inflammation to destruction of the mucosa of the intestine to fatal exfoliation of intestinal epithelial calls. Inflammation typically presents as fever, abdominal pain, nausea, vomiting, diarrhea, intestinal bleeding, and jaundice.

The method of the present invention employs oral administration of a propylactically effective amount of a topically active corticosteroid (TAC) to a patient having undergone hematopoietic cell or organ allograft transplantation. Representative TACs include, but are not limited to, beclomethasone dipropionate, alclometasone dipropionate, busedonide, 22S busesonide, 22R budesonide, beclomethasone-17-monopropionate, clobetasol propionate, diflorasone diacetate, flunisolide, flurandrenolide, fluticasone propionate, halobetasol propionate, halcinocide, mometasone furoate, and triamcinalone acetonide. Such TACs are well known to those skilled in the field of, for example, intestinal disorders, and are commercially available from any number of sources. Suitable TACs of this invention have rapid first-pass metabolism in the intestine and liver, low systemic bioavailability, high topical activity, and rapid excretion (see, e.g., Thiesen et al., *Alimentary Pharmacology & Therapeutics* 10:487–496, 1996) (incorporated herein by reference).

In one embodiment of this invention, the TAC is beclomethasone dipropionate (BDP). BDP is a compound which is available from a number of commercial sources, such as Schering-Plough Corporation (Kenilworth, N.J.) in bulk crystalline form, and has the following structure (i.e., beclomethasone 17,21-dipropionate):

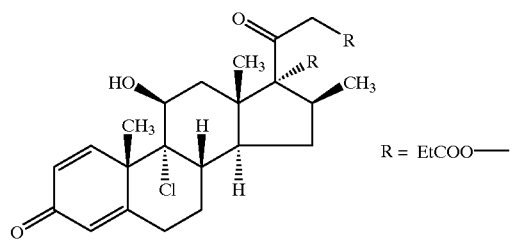

R = EtCOO—

Patients having undergone hematopoietic cell or organ allograft transplantation, and which may thus be administered a TAC according to this invention, are allogenic hematopoietic cell recipients who have typically received marrow-ablative chemotherapy and/or total body irradiation followed by donor hematopoietic cell infusion, or patients having undergone intestinal or liver transplantation. Such procedures have been widely disclosed, and are well known to those skilled in this field.

Such patients receive a prophylactically acceptable amount of a TAC by oral administration. The TAC may be formulated for oral administration by techniques well known in the formulation field, including formulation as a capsule, pill, coated microsphere with specific dissolution qualities, or emulsion. Suitable capsules or pills generally contain from 1 mg to 2 mg TAC, and typically about 1 mg TAC, plus optional fillers, such as lactose, and may be coated with a variety of materials, such as cellulose acetate phthalate. By appropriate coating, such capsules, microspheres or pills may be made to dissolve within various location of the intestinal tract. For example, enteric-coated capsules prepared with a coating of cellulose acetate phthalate are known to dissolve in the alkaline environment of the small bowel, thus delivering its content to the small bowel and colon. Emulsions containing a TAC may also be employed for oral delivery, including optional emulsifying agents.

In addition to the TAC, prophylactically acceptable carriers and/or diluents may be employed and are familiar to those skilled in the art. Formulations in the form of pills, capsules, microspheres, granules or tablets may contain, in addition to one or more TACs, diluents, dispersing and surface active agents, binders and lubricants. One skilled in the art may further formulate the TAC in an appropriate manner, and in accordance with accepted practices, such as those disclosed in *Remington's Pharmaceutical Sciences*, Gennaro, Ed., Mack Publishing Co., Easton, Pa., 1990 (incorporated herein by reference).

In the practice of this invention, a "prophylactically effective amount" of a TAC is administered to a patient in need thereof. In general terms, a prophylactically effective amount of a TAC is an amount which, when delivered orally, prevents, delays and/or reduces the severity of the symptoms associated with GVHD following hematopoietic cell transplantation, or associated with HVGD following organ allograft transplantation. Such an amount may be readily determined by one skilled in the art by well known dose-response investigations, and will generally range from 4 mg/day to 12 mg/day, and more typically range from 6 mg/day to 8 mg/day.

As optional components, other active prophylactic agents may be administered in combination with the TAC, including (but not limited to) cyclosporine, methotrexate, tacrolimus and biological agents that affect T-lymphocytes.

In the context of GVHD, preventative administration of a TAC begins after infusion of hematopoietic cells, but before engraftment of these cells, and continues for a period of time prior to the presentation of symptoms associated with GVHD. Once symptoms are presented by a patient, prophylactic use of a TAC would no longer be warranted, and use in the context of a treatment regimen would begin (optionally in combination with other active agents). Use of a TAC within a treatment regimen is not encompassed within the scope of this invention.

As for HVGD, preventative administration of a TAC begins after organ allograft transplantation, and continues for a period of time prior to the presentation of symptoms associated with HVGD. Once symptoms are presented by a patient, prophylactic use of a TAC would no longer be warranted, and use in the context of a treatment regimen would begin (optionally in combination with other active agents).

An important aspect of this invention is that the TAC is orally administered such that it is topically administered to the intestinal and/or liver tissue. Thus, oral administration, as that term is used herein, is not intended to encompass systemic administration, such as by intravenous injection. Rather, the TAC has little (if any) systemic availability, but high topical activity on intestinal and/or liver tissue. Such limited distribution results in fewer side effects, which is a significant advantage of this invention.

In addition to differences with regard to location and timing of administration, there is also a biological basis between prophylactic administration and treatment. In prophylaxis, the objective is to achieve tolerance for hematopoietic precursor cells and their progeny, or an organ allograft. In this context, "tolerance" means a phenomenon whereby the immune system is modified to accept "foreign" cells and proteins without rejecting them. Another objective in prophylaxis is to prevent the initiation of a cascade of biological events that result in tissue destruction. In treatment, the objectives are to suppress a wide variety of biological events that have already resulted in tissue destruction, for example, the generation of inflammatory cytokines, the recruitment of additional inflammatory cells to the site of injury, the destruction of the barrier function of the intestinal mucosa (the lining), the passage of bacteria and toxins through the damaged intestinal mucosa, the up-regulation of biologic responses to bacteria and endotoxin, and the widespread organ responses to these events (such as leaky blood vessels, increased cardiac output, decreased systemic vascular resistance, diffuse lung injury, and renal insufficiency). When a patient has GVHD, treatment is successful only 50–75% of the time; the remainder of the patients generally die. This is why prevention (as opposed to treatment) is critical in the context of GVHD following hematopoietic cell transplantation. HVGD involving a transplanted intestine or liver presents similar concerns.

In the practice of this invention, it is believed that oral administration of a TAC is effective as prophylaxis because the initiating event in GVHD is the recognition of host epithelial cells that line the intestine by allogeneic donor lymphocytes, while the initiating event in HVGD is recognition of epithelial cells in the transplanted intestine by host lymphocytes. By appropriate formulation of the TAC (such as enterically coated capsules), it can be delivered to all of the mucosal surface of the intestine in high doses. Thus, the TAC can achieve high concentrations in the intestinal mucosa where this initiating alloimmune recognition event is taking place. It is believed that blunting the initiating event prevents the large cascade of biologic events that make up the syndromes of GVHD and HVGD.

With regard to preventing liver damage from either GVHD or HVGD post-liver transplantation, the orally administered TAC is either metabolized by the epithelial cells lining the intestinal tract, or is delivered intact directly to the liver. The intestine is unique in that its draining venous blood supply does not go directly back to the heart, but rather is routed through the liver via the portal circulation. One important organ affected by acute GVHD and HVGD is the liver, where epithelial cells that form bile ducts are targets of donor lymphocytes. Accordingly, oral TAC (and/or its active metabolites) will be delivered directly to the liver in sufficiently high concentration to have the same effect on donor lymphocytes within the liver as discussed above in the context of in intestinal mucosa, thereby preventing destruction of bile duct cells and thus the onset of liver GVHD post-hematopoietic cell transplantation and HVGD post-liver transplantation.

The following examples are offered by way of illustration, not limitation.

EXAMPLE

Example 1

A patient with an underlying disease is treated for that disease with a form of therapy that includes the intravenous infusion of hematopoietic cells from an allogeneic donor. Within two days after the donor hematopoietic cells have been infused, the patient takes by mouth medication in the form of eight capsules of BDP per day, 1 mg per capsule, half of which are plain gelatin capsules that dissolve in acidic stomach fluid, the other half being gelatin capsules coated with a material that dissolves in the alkaline fluid of the small intestine and/or colon. The BDP capsules are taken on a daily basis (eight per day) for 80 days following the infusion of the hematopoietic cells. After the 80 day period is over, the daily dose of BDP capsules is decreased by 50% for the ensuing 7 days (i.e., four capsules per day), then by an additional 50% for the next 7 days (i.e., two capsules per day), and then discontinued.

Example 2

A patient with a serious intestinal disease (infarction of the intestine following disruption of blood flow) is treated for that disease with a form of therapy that includes the transplantation of intestine from another person who is not related to the patient. After the operation, the patient takes (by mouth) medication in the form of eight capsules of BDP per day, 1 mg per capsule, where each capsule is coated with a material that dissolves in the alkaline fluid of the transplanted intestine. The BDP capsules are taken on a daily basis (8 per day) for 90 days, and then decreased by 50%, to a dose of 4 capsules per day which would be taken indefinitely to prevent host-versus-graft-disease, or rejection of the transplanted intestine.

It will be appreciated that, although specific embodiments of this invention have been described herein for purpose of illustration, various modifications may be made without departing from the spirit and scope of the invention.

I claim:

1. A method for preventing tissue damage associated with graft-versus-host disease in a patient having undergone hematopoietic cell transplantation, comprising orally administering to the patient a prophylactically effective amount of a topically active corticosteroid for a period of time following allogenic hematopoietic cell transplantation and prior to the presentation of symptoms associated with graft-versus-host disease.

2. The method of claim 1 wherein the topically active corticosteroid is administered orally at a dosage of 4 mg per day to 12 mg per day.

3. The method of claim 1 wherein the tissue is intestinal mucosa.

4. The method of claim 1 wherein the tissue is small bile ducts in the liver.

5. The method of claim 1 wherein the tissue damage is inflammation.

6. The method of claim 1 wherein the tissue damage is destruction of the mucosa of the intestine.

7. The method of claim 1 wherein the topically active corticosteroid is formulated for oral administration in the form of a pill, capsule or microsphere.

8. The method of claim 7 wherein the of topically active corticosteroid is formulated such that the pill, microsphere, or capsule dissolves in the stomach, small intestine or colon.

9. The method of claim 1 wherein the topically active corticosteroid is formulated for oral administration in the form of an emulsion.

10. The method of claim 1 wherein administration of the topically active corticosteroid initiates following infusion of the hematopoietic cells.

11. The method of claim 1 wherein administration of the topically active corticosteroid ceases after 80 days following infusion of the hematopoietic cells.

12. The method of claim 1 wherein the patient is the recipient of HLA-mismatched hematopoietic stem cells.

13. The method of claim 1 wherein the patient is the recipient of unrelated donor hematopoietic stem cells, umbilical vein hematopoietic stem cells, or peripheral blood stem cells.

14. The method of claim 1 wherein the topically active corticosteroid is administered in combination with other prophylactic agents.

15. The method of claim 1 wherein the topically active corticosteroid is beclomethasone dipropionate.

16. The method of claim 1 wherein the topically active corticosteroid is alclometasone dipropionate, busedonide, 22S busesonide, 22R budesonide, beclomethasone-17-monopropionate, clobetasol propionate, diflorasone diacetate, flunisolide, flurandrenolide, fluticasone propionate, halobetasol propionate, halcinocide, mometasone furoate, or triamcinalone acetonide.

17. A method for preventing intestinal inflammation associated with intestinal graft-versus-host disease in a patient having undergone hematopoietic cell transplantation, comprising orally administering to the patient a prophylactically effective amount of beclomethasone dipropionate for a period of time following hematopoietic cell transplantation and prior to the presentation of symptoms of intestinal inflammation associated with intestinal graft-versus-host disease.

18. The method of claim 17 wherein the beclomethasone dipropionate is administered orally at a dosage of 4 mg per day to 12 mg per day.

19. The method of claim 17 wherein the beclomethasone dipropionate is formulated for oral administration in the form of a pill, capsule or microsphere.

20. The method of claim 19 wherein the pill, capsule or microsphere dissolves in the stomach, small intestine or colon.

21. The method of claim 17 wherein the beclomethasone dipropionate is formulated for oral administration in the form of an emulsion.

22. The method of claim 17 wherein administration of beclomethasone dipropionate initiates following infusion of the hematopoietic cells.

23. The method of claim 17 wherein administration of beclomethasone dipropionate ceases after 80 days following infusion of the hematopoietic cells.

24. The method of claim 17 wherein the patient is the recipient of HLA-mismatched hematopoietic stem cells.

25. The method of claim 17 wherein the patient is the recipient of unrelated donor hematopoietic stem cells, umbilical vein hematopoietic stem cells or peripheral blood stem cells.

26. The method of claim 17 wherein the beclomethasone dipropionate is administered in combination with other prophylactic agents.

27. A method for preventing tissue damage associated with host-versus-graft disease in a patient having undergone intestinal or liver transplantation, comprising orally administering to the patient a prophylactically effective amount of a topically active corticosteroid for a period of time following intestinal or liver transplantation and prior to the presentation of signs or symptoms associated with host-versus-graft disease.

28. The method of claim 27 wherein the topically active corticosteroid is administered orally at a dosage of 4 mg per day to 12 mg per day.

29. The method of claim 27 wherein the tissue is intestinal mucosa.

30. The method of claim 27 wherein the tissue is small bile ducts in the liver.

31. The method of claim 27 wherein the tissue damage is inflammation.

32. The method of claim 27 wherein the tissue damage is destruction of the mucosa of the intestine.

33. The method of claim 27 wherein the topically active corticosteroid is formulated for oral administration in the form of a pill, microsphere or capsule.

34. The method of claim 33 wherein the of topically active corticosteroid is formulated such that the pill, microsphere, or capsule dissolves in the stomach, small intestine or colon.

35. The method of claim 27 wherein the topically active corticosteroid is formulated for oral administration in the form of an emulsion.

36. The method of claim 27 wherein administration of the topically active corticosteroid initiates immediately following intestinal or liver transplantation.

37. The method of claim 27 wherein administration of the topically active corticosteroid continues following intestinal or liver transplantation.

38. The method of claim 27 wherein the topically active corticosteroid is administered in combination with other prophylactic agents.

39. The method of claim 27 wherein the topically active corticosteroid is beclomethasone dipropionate.

40. The method of claim 27 wherein the topically active corticosteroid is alclometasone dipropionate, busedonide, 22S busesonide, 22R budesonide, beclomethasone-17-monopropionate, clobetasol propionate, diflorasone diacetate, flunisolide, flurandrenolide, fluticasone propionate, halobetasol propionate, halcinocide, mometasone furoate, or triamcinalone acetonide.

* * * * *